(12) United States Patent
Grichnik

(10) Patent No.: US 11,331,062 B2
(45) Date of Patent: *May 17, 2022

(54) MOBILE X-RAY IMAGING APPARATUS

(71) Applicant: James A Grichnik, Hawthornwoods, IL (US)

(72) Inventor: James A Grichnik, Hawthornwoods, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/387,612

(22) Filed: Jul. 28, 2021

(65) Prior Publication Data

US 2021/0353239 A1 Nov. 18, 2021

Related U.S. Application Data

(63) Continuation-in-part of application No. 17/129,879, filed on Dec. 21, 2020, now Pat. No. 11,191,500.

(60) Provisional application No. 63/124,638, filed on Dec. 11, 2020, provisional application No. 62/951,766, filed on Dec. 20, 2019.

(51) Int. Cl.
*A61B 6/00* (2006.01)
*A61B 6/04* (2006.01)

(52) U.S. Cl.
CPC .......... *A61B 6/4405* (2013.01); *A61B 6/0407* (2013.01); *A61B 6/46* (2013.01); *A61B 6/487* (2013.01)

(58) Field of Classification Search
CPC ....... A61B 6/548; A61B 6/4423; A61B 6/102; A61B 6/4441; A61B 6/547; A61B 6/4225; A61B 6/4007; A61B 6/032; A61B 6/447; A61B 6/4411; A61B 6/4452; G06T 2207/10116

See application file for complete search history.

(56) References Cited

U.S. PATENT DOCUMENTS

| | | |
|---|---|---|
| 5,586,162 A | 12/1996 | Grichnik |
| 2020/0163634 A1* | 5/2020 | Turner ................. A61B 6/4441 |

* cited by examiner

*Primary Examiner* — Don K Wong

(57) ABSTRACT

A mobile X-ray imaging apparatus is an apparatus that enables the performance of a fluoroscopic procedure in any setting. The apparatus may include an elongated frame, a wheeled base, a U-shaped support, a height-adjusting track, a support carriage, an X-ray generator, and an image-capturing device. The elongated frame supports the U-shaped support and maintains the U-shaped support at a desired height. The wheeled base maintains the elongated frame upright and facilitates the relocation of the apparatus. The U-shaped support maintains the X-ray generator and the image-capturing device at the desired arrangement to perform the fluoroscopic procedure. The height-adjusting track enables the repositioning of the U-shaped support along the elongated frame to accommodate the patient. The support carriage connects the U-shaped support to the height-adjusting track and keeps the U-shaped support in place during the procedure. The X-ray generator and the image-capturing device enable the fluoroscopic procedure to be performed.

20 Claims, 11 Drawing Sheets

MOBILE X-RAY IMAGING APPARATUS

The current application is a continuation-in-part (CIP) application of a U.S. non-provisional application Ser. No. 17/129,879 filed on Dec. 21, 2020. The U.S. non-provisional application Ser. No. 17/129,879 claims a priority to a U.S. provisional application Ser. No. 62/951,766 filed on Dec. 20, 2019.

The current application also claims a priority to a U.S. provisional application Ser. No. 63/124,638 filed on Dec. 11, 2020.

FIELD OF THE INVENTION

The present invention generally relates to the field X-ray imaging apparatuses, reciting a structural and functional improvement to conventional fluoroscopy units. More specifically, the present invention is a self-supporting, modular fluoroscopy unit that may be deployed to under-supported areas lacking the necessary infrastructure to support a conventional fluoroscopy unit.

BACKGROUND OF THE INVENTION

Fluoroscopy broadly refers to an X-ray imaging process where a continuous image, similar to a video, of a moving part of the body is taken. To facilitate the study of the joints, radiopaque contrast agents may be swallowed, injected, or otherwise inserted into a patient to delineate borders between tissues. A common fluoroscopic procedure is the video fluoroscopic swallow study (VFSS), sometimes referred to as a modified barium swallow (MBS) or esophogram. This procedure is immensely useful in diagnosing and assessing pharyngeal dysphagia—a reduction in swallowing function commonly stemming from stroke, brain bleeds, head trauma, degenerative neurologic diseases, aspiration pneumonia, a tracheostomy, and now COVID-19 related deficits. VFSS enables a medical practitioner to evaluate the anatomy and physiology of the oral cavity, pharynx, and esophagus to assess the patient's swallowing action to inform recommendations for future treatment, such as informing recommendations on food and liquid consistencies compatible with a patient, guiding compensatory strategies for reduced muscular function, and developing attainable treatment goals. This type of imaging procedure is commonplace in most well-equipped medical facilities as approximately 1 in 25 people will experience dysphagia in their lifetime, with 22% of those people being age 50 and older.

However, the conventional VFSS procedure is not a simple or painless process. Nearly all patients suffering from dysphagia also often have some form of immobility, requiring a wheelchair or other assistance. Conventional VFSS units are not equipped or configured to accept standard-sized wheelchairs, requiring a technician to transfer the patient into a special 'swallow chair' compatible with the scanning unit. The swallow chairs are specialized equipment—frequently unavailable or in poor conditions given the limitations of their use and the exorbitant cost of repair or replacement. This compounds the discomfort caused by the transfer from the wheelchair to the swallow chair, in addition to increasing the risk of injury to the patient and technician. The transfer process is a needless complication of an otherwise painless process; multiple personnel should not be required for this routine process, nor should a patient be discomforted due to an avoidable equipment incompatibility. In edge cases, large patients (bariatric, broad-shouldered, or otherwise) may also require specialized equipment to perform a VFSS due to the limited scanning range of conventional units. Claustrophobic patients may also have issues with the procedure using conventional equipment—antero-posterior scans may not be able to be taken with the limited space and the mobility of the scanning equipment. To overcome the technical limitations of conventional equipment, surgical scanning units are occasionally utilized. However, this is subject to the availability of the C-arm unit and is not an optimal solution as the positioning of both scanning units within the same radiology suite severely cramps the working area for any medical personnel as well as the patient.

It is therefore an objective of the present invention to provide a more convenient conventional fluoroscopy machine that utilizes a modular, expanded conventional scanning structure which enables a patient to remain seated in a conventional wheelchair throughout the imaging procedure. The use of this open-concept construction greatly expands the scannable area of the proposed unit, thus reducing patient anxiety and eliminating the need for a specialized chair. Another objective of the present invention is to provide a scanning structure that may be rotated to accommodate patients laid on a table or gurney, combining the functionality of two conventional scanning units into one. Further, another objective of the present invention is to provide a mechanism that uses low-wattage and is lightweight to facilitate the packaging, shipment, and deployment of the present invention into facilities that are typically unable to support fluoroscopic imaging (e.g., remote medical outposts relying on unstable power grids). The functionality of the present invention may be further expanded with the introduction of interchangeable detector heads, integrated power supplies, manual redundant positioning mechanisms, and telemedicine features across various conceivable embodiments.

SUMMARY OF THE INVENTION

The present invention is a mobile X-ray imaging apparatus designed to accommodate patients in a variety of situations. For example, the present invention can accommodate patients in a wheelchair or on a gurney without having to move the patient from the wheelchair or the gurney to the apparatus during the procedure. However, the present invention can also be utilized for veterinary applications. The present invention is mobile enough to easily pass through a 48-inch door so that the apparatus can be used anywhere inside a facility. The present invention can utilize fluoroscopic or X-ray film units without requiring the use of a shielded room so that the present invention can be utilized in different locations. The present invention also utilizes ultralow doses of radiation, which eliminates the need for personal shielding on the patient within five feet of the radiation source. Further, the present invention requires no installation, just a power source such as a 110 Volt wall plug.

The present invention aims to provide an improved iteration of a fluoroscopic scanning unit, comprising vertical and lateral adjustment mechanisms that enable a patient or subject to be seated or stay supine during a scanning procedure. Further, the present invention features a novel, modular construction to enable the disassembly and redeployment of the present invention to remote facilities. At least one embodiment of the present invention includes an integral power supply, including a means of integrating external renewable sources of power.

DETAIL DESCRIPTIONS OF THE INVENTION

All illustrations of the drawings are for the purpose of describing selected versions of the present invention and are not intended to limit the scope of the present invention.

Figure 1:
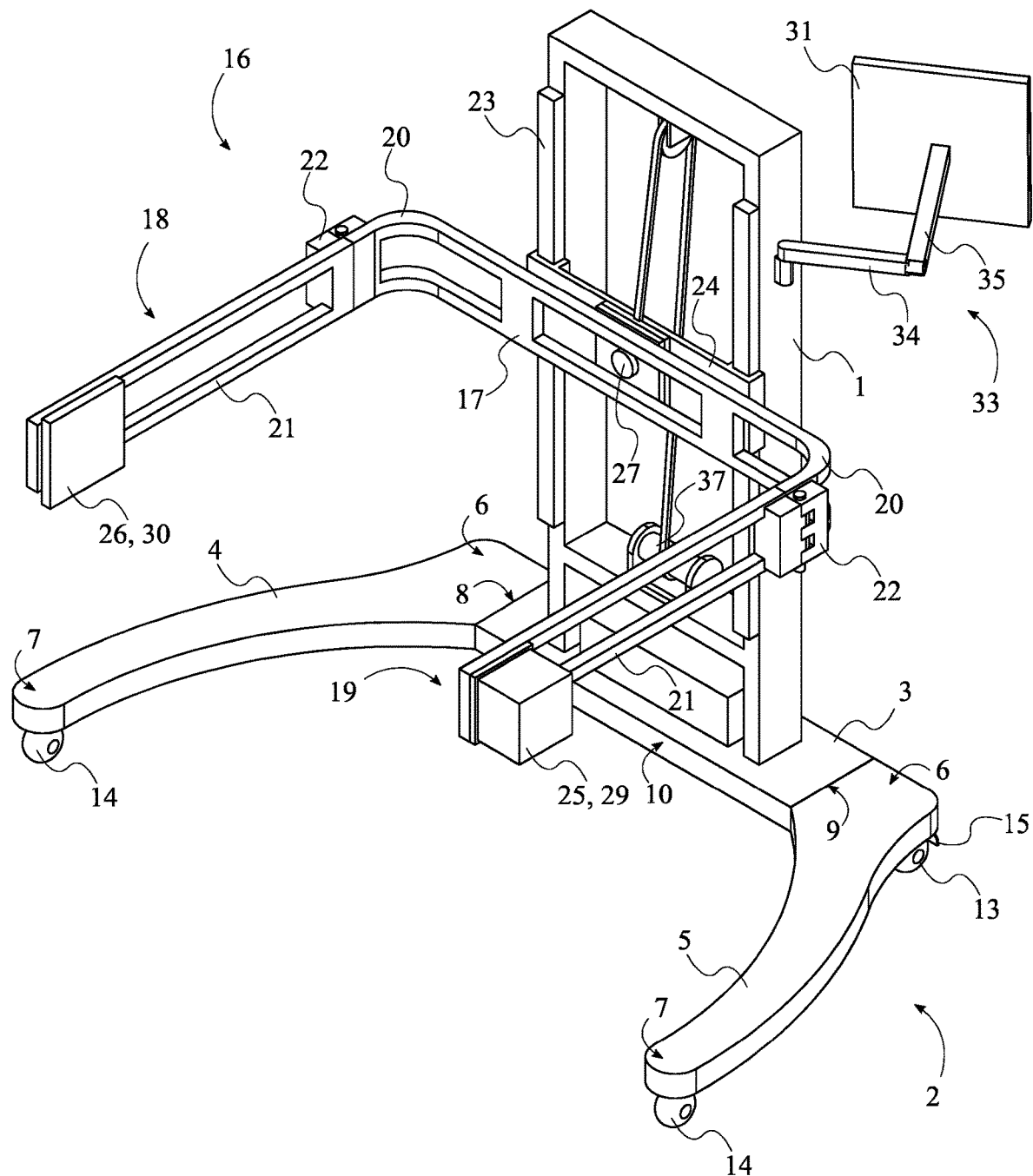
FIG. 1 is a top-front-left perspective view of the present invention, wherein the present invention is shown without a housing.
Figure 2:
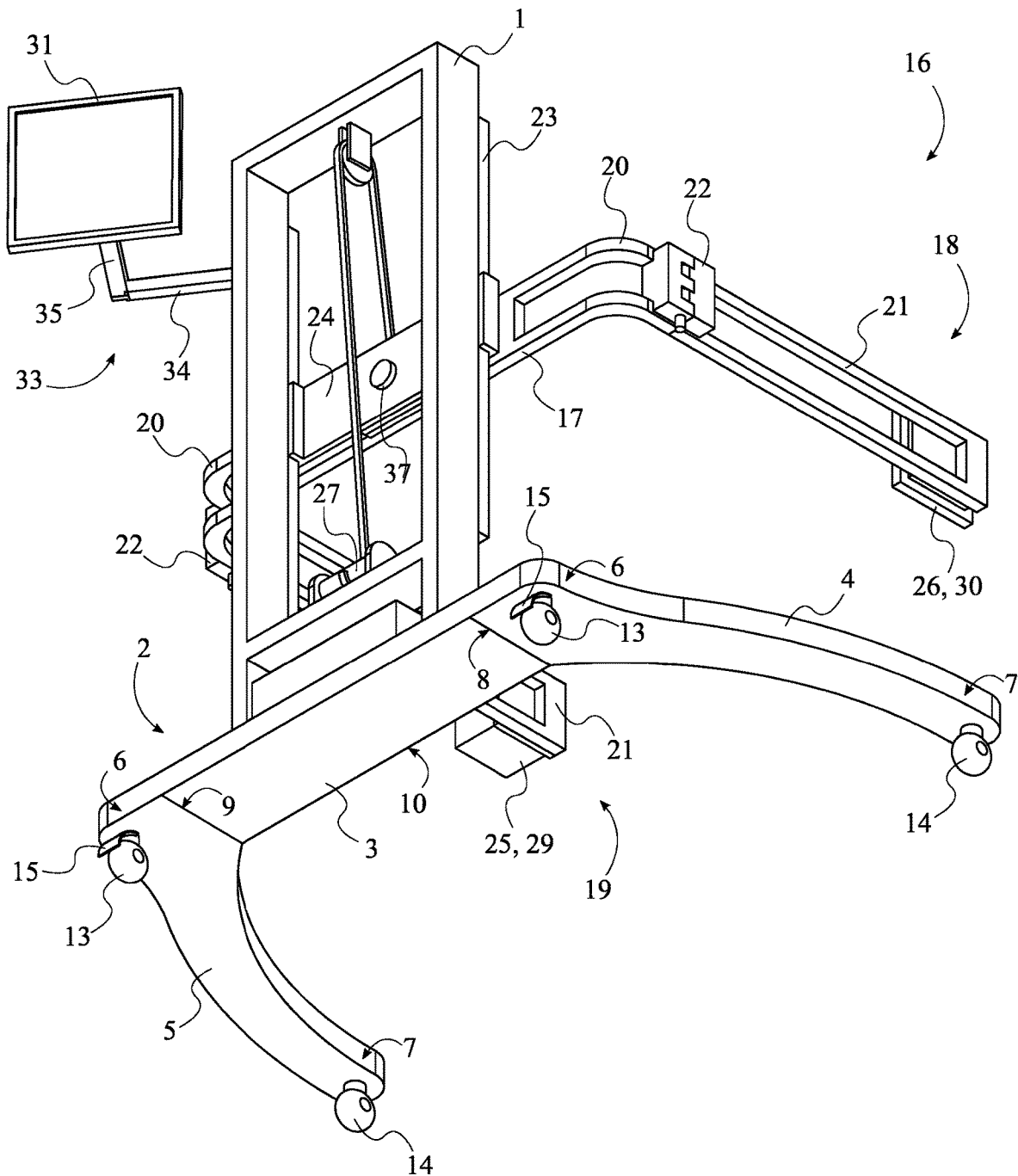
FIG. 2 is a top-rear-right perspective view of the present invention.

The present invention is a mobile X-ray imaging apparatus that enables medical professionals to perform a fluoroscopic procedure on a patient in any setting within a medical facility. In a preferred embodiment, the present invention may comprise an elongated frame 1, a wheeled base 2, a U-shaped support 16, a height-adjusting track 23, a support carriage 24, an X-ray generator 25, and an image-capturing device 26. As can be seen in FIGS. 1 and 2, the elongated frame 1 supports the load from the U-shaped support 16 and maintains the U-shaped support 16 at a desired height from the ground. The wheeled base 2 maintains the elongated frame 1 in an upright orientation and facilitates the relocation of the present invention. The U-shaped support 16 maintains the X-ray generator 25 and the image-capturing device 26 at the desired configuration to perform the fluoroscopic procedure on the patient. The height-adjusting track 23 enables the repositioning of the U-shaped support 16 along the elongated frame 1 to the desired height to accommodate the patient. The support carriage 24 connects the U-shaped support 16 to the height-adjusting track 23 and maintains the desired configuration of the U-shaped support 16 during the procedure. The X-ray generator 25 and the image-capturing device 26 enable the medical staff to perform the fluoroscopic procedure on the patient.

Figure 3:
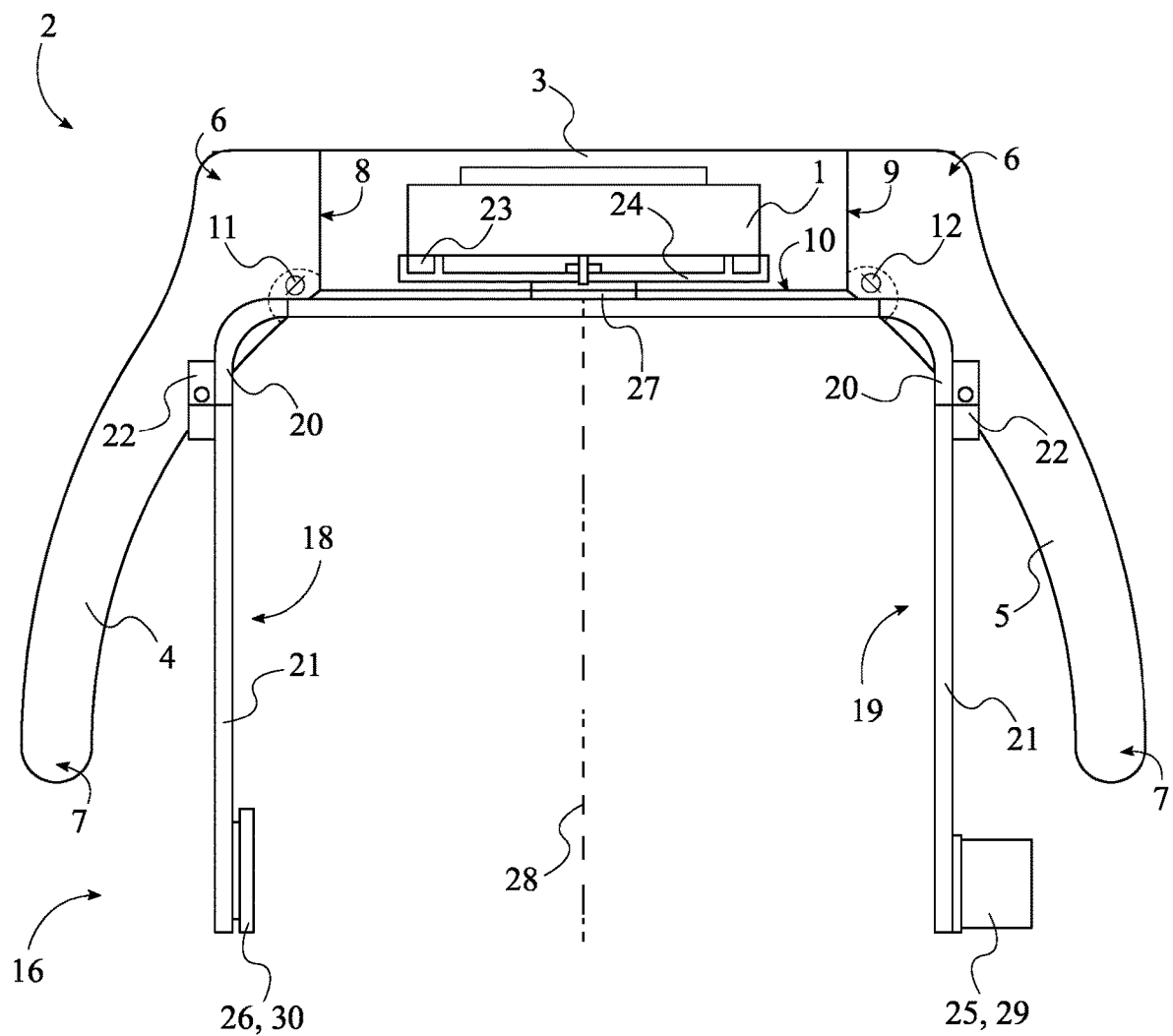
FIG. 3 is a top view of the present invention, wherein the user interface and the foldable arm are shown removed.

The general configuration of the aforementioned components enables the patient to be seated or stay supine during the fluoroscopic procedure without the need for additional support medical furniture. The present invention features a novel, modular construction to enable the disassembly and redeployment of the present invention to remote facilities. As can be seen in FIG. 1 through 3, the wheeled base 2 is designed to facilitate the transportation of the present invention and prevents the elongated frame 1 from falling over due to the load from the U-shaped support 16. The wheeled base 2 comprises a base platform 3, a first bracketing arm 4, and a second bracketing arm 5. The base platform 3 supports the load from the elongated frame 1 and maintains the elongated frame 1 elevated to facilitate the transportation of the present invention. The first bracketing arm 4 and the second bracketing arm 5 help balance the whole structure to prevent the elongated from tipping sideways or forwards. In addition, the U-shaped support 16 comprises a support web 17, a first support arm 18, and a second support arm 19. The support web 17 connects the first support arm 18 and the second support arm 19 to the support carriage 24. The first support arm 18 and the second support arm 19 keep the X-ray generator 25 and the image-capturing device 26, respectively, at a desired configuration during the fluoroscopic procedure. The first bracketing arm 4 is connected adjacent to the base platform 3 to secure the first bracketing arm 4 to the base platform 3. Similarly, the second bracketing arm 5 is connected adjacent to the base platform 3, opposite to the first bracketing arm 4, to secure the second bracketing arm 5 to the base platform 3. The base platform 3 is also terminally mounted to the elongated frame 1 to secure the elongated frame 1 to the base platform 3. This arrangement of the first support arm 18 and the second support arm 19 provides wide lateral support to the base platform 3, thus preventing the elongated frame 1 on the base platform 3 from tilting forward or sideways.

Furthermore, the height-adjusting track 23 is laterally mounted along the elongated frame 1 to enable the movement of the U-shaped support 16 along the elongated frame 1, as can be seen in FIGS. 1, 2, 5, and 6. Thus, the user can adjust the height of the U-shaped support 16 to accommodate the position of the patient on a wheelchair or on a bed. The first support arm 18 is terminally connected to the support web 17. Likewise, the second support arm 19 is terminally connected to the support web 17, opposite to the first support arm 18, to form the U shape of the U-shaped support 16 along with the first support arm 18. The support web 17 is movably mounted to the height-adjusting track 23 by the support carriage 24 so that the user can choose the position of the support web 17 along the height-adjusting track 23 to adjust the height of the U-shaped support 16. Furthermore, the X-ray generator 25 is laterally mounted to the first support arm 18, offset from the support web 17, to emit X-rays to be utilized to visualize in real-time the desired internal body areas. On the other hand, the image-capturing device 26 is laterally mounted to the second support arm 19, offset from the support web 17, to capture the emitted X-rays to generate the live imaging of the patient. In some embodiments, the height-adjusting track 23 can be a manually operated mechanism that the user can engage to manually move the support carriage 24 along the height-adjusting track 23. For example, a gear assembly may be operatively integrated into the height-adjusting track 23 to move the support carriage 24 along the height-adjusting track 23. A hand crank may be operatively connected to the gear assembly so that the user can manually engage the gear assembly. In other embodiments, an automated mechanism may be integrated into the height-adjusting track 23 to automatically move the support carriage 24 along the height-adjusting track 23 to a desired location. For example, a set of linear actuators or a hydraulics system may be operatively integrated into the height-adjusting track 23 to move the support carriage 24 along the height-adjusting track 23 to a predetermined location.

As previously discussed, the wheeled base 2 is designed to prevent the present invention from tipping over. As can be seen in FIG. 1 through 3, the base platform 3 may further comprise a first widthwise edge 8 and a second widthwise edge 9 preferably corresponding to the lateral edges of the base platform 3. The first bracketing arm 4 and the second bracketing arm 5 each comprises a proximal bracketing end 6 and a distal bracketing end 7 due to the elongated structure of each bracketing arm. The proximal bracketing end 6 of the first bracketing arm 4 is connected adjacent to the first widthwise edge 8 to connect the first bracketing arm 4 to the base platform 3. The distal bracketing end 7 of the first bracketing arm 4 is positioned offset from the first widthwise edge 8 to orient the first bracketing arm 4 away from the base platform 3. Likewise, the proximal bracketing end 6 of the second bracketing arm 5 is connected adjacent to the second widthwise edge 9 to connect the second bracketing arm 5 to the base platform 3. The distal bracketing end 7 of the second bracketing arm 5 is positioned offset from the second widthwise edge 9 to orient the second bracketing arm 5 away from the base platform 3. Further, the first bracketing arm 4 and the second bracketing arm 5 are positioned adjacent to the U-shaped support 16 to prevent the present invention from tipping forward due to the load of the U-shaped support 16.

In addition, the first bracketing arm 4 and the second bracketing arm 5 can be arranged to cover a wide area for greater stability of the present invention. As can be seen in FIG. 1 through 3, the base platform 3 may further comprise a first lengthwise edge 10 preferably corresponding to the longer edge of the base platform 3 adjacent to the U-shaped support 16. The first bracketing arm 4 is oriented at a first obtuse angle 11 with the first lengthwise edge 10 to provide lateral support to the base platform 3. Likewise, the second bracketing arm 5 is oriented at a second obtuse angle 12 with the first lengthwise edge 10 to the provide lateral support to the base platform 3. The first obtuse angle 11 and the second obtuse angle 12 are also preferable the same angle to create a symmetrical wheeled base 2. Thus, the base platform 3 is a stable structure that prevents the present invention from easily tipping over. In other embodiments, the wheeled base 2 can be designed as slim structure to further facilitate the relocation of the present invention through narrower spaces.

Figure 5:
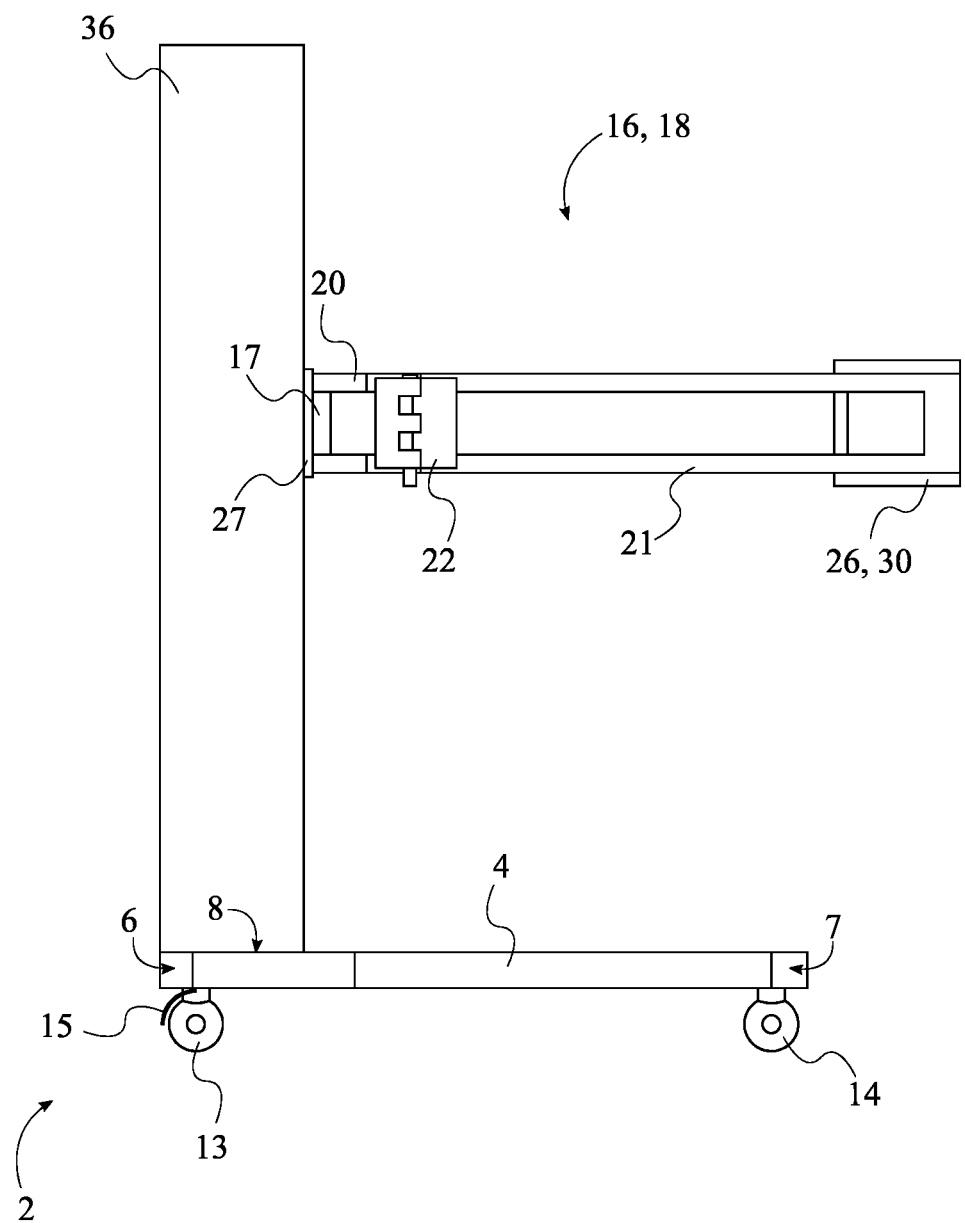
FIG. 5 is a side view of the present invention, wherein the housing is shown.
Figure 6:
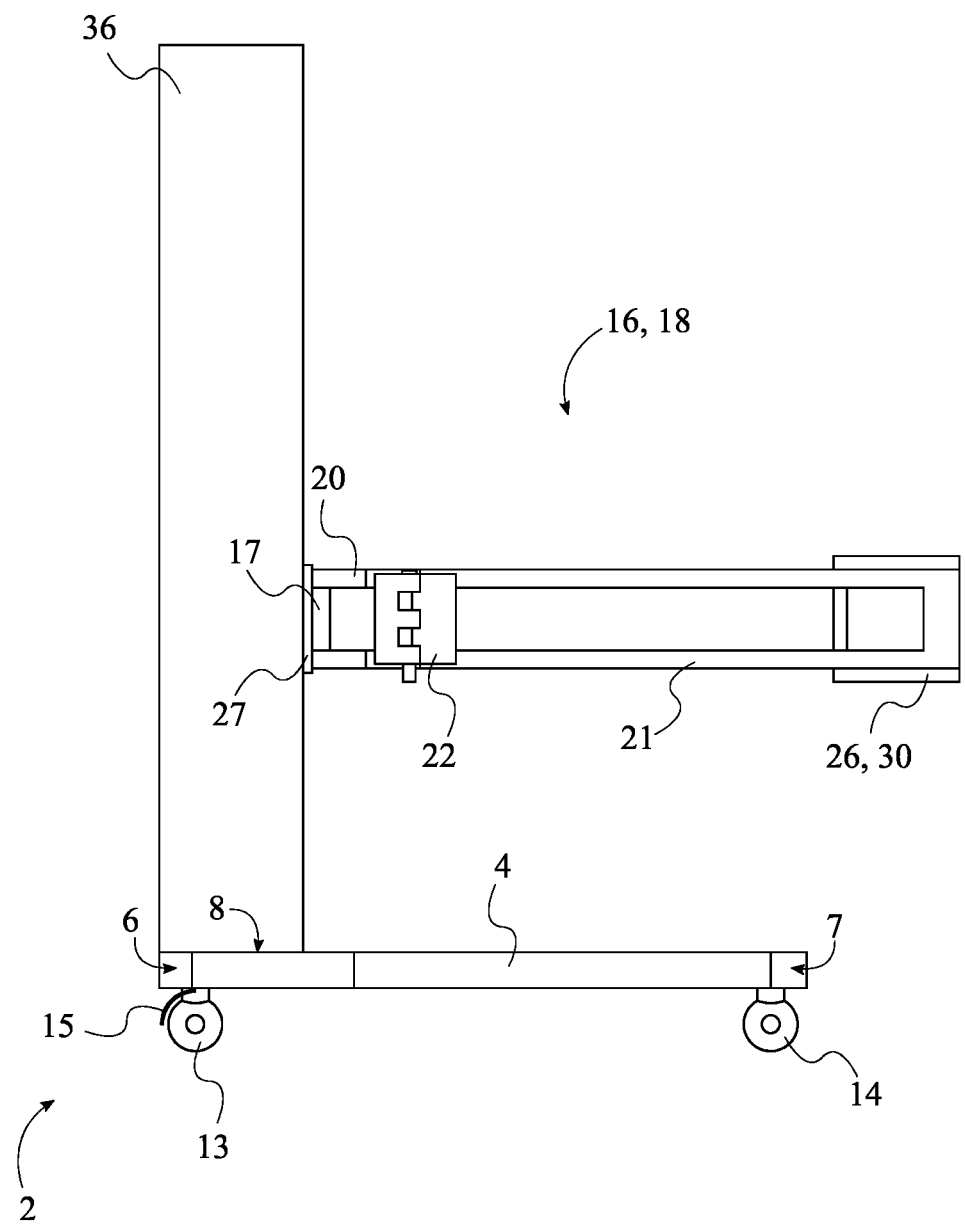
FIG. 6 is a side view of the present invention, wherein the U-shaped support is shown lowered.

When the present invention has been moved to the desired location, the present invention may be locked into position to prevent accidental movement of the wheeled base 2 during the fluoroscopic procedure. To do so, the present invention may further comprise a wheel-lock mechanism 15. As can be seen in FIGS. 5 and 6, the wheeled base 2 may also comprise a pair of drive wheels 13 to facilitate the movement of the wheeled base 2. The pair of drive wheels 13 enable the user to roll the present invention around the facility without the need of other tools such as a hand truck. In addition, the wheel-lock mechanism 15 is operatively integrated into the pair of drive wheels 13, wherein the wheel-lock mechanism 15 is used to prevent the rotation of the pair of drive wheels 13. For example, the wheel-lock mechanism 15 can be a manual brake such as a foot-activated swivel lock on each drive wheel that can be selectively engaged to lock the pair of drive wheels 13 in place. In other embodiments, the wheel-lock mechanism 15 can also include a spring-loaded lever positioned on the elongated frame 1 that can be used to remotely engage the wheel-lock mechanism 15.

In addition to the pair of drive wheels 13, the wheeled base 2 may further comprise a plurality of casters 14 to ease the load on the pair of drive wheels 13. As can be seen in FIGS. 5 and 6, the plurality of casters 14 further increases the stability of the present invention when the present invention is being moved around. The plurality of casters 14 is positioned offset from the pair of drive wheels 13 to maintain the balance of the wheeled base 2. The plurality of casters 14 is also positioned adjacent to the U-shaped support 16 to spread out the load on the plurality of casters 14 and the pair of drive wheels 13. For example, a caster of the plurality of casters 14 can be positioned adjacent to the distal bracketing end 7 of the first bracketing arm 4. Similarly, another caster of the plurality of casters 14 can be positioned adjacent to the distal bracketing end 7 of the second bracketing arm 5. Thus, the wheeled base 2 is stable by spreading the load on all wheels, and the user does not have to worry about the present invention tipping over during transportation or during the fluoroscopic procedure.

Figure 4:
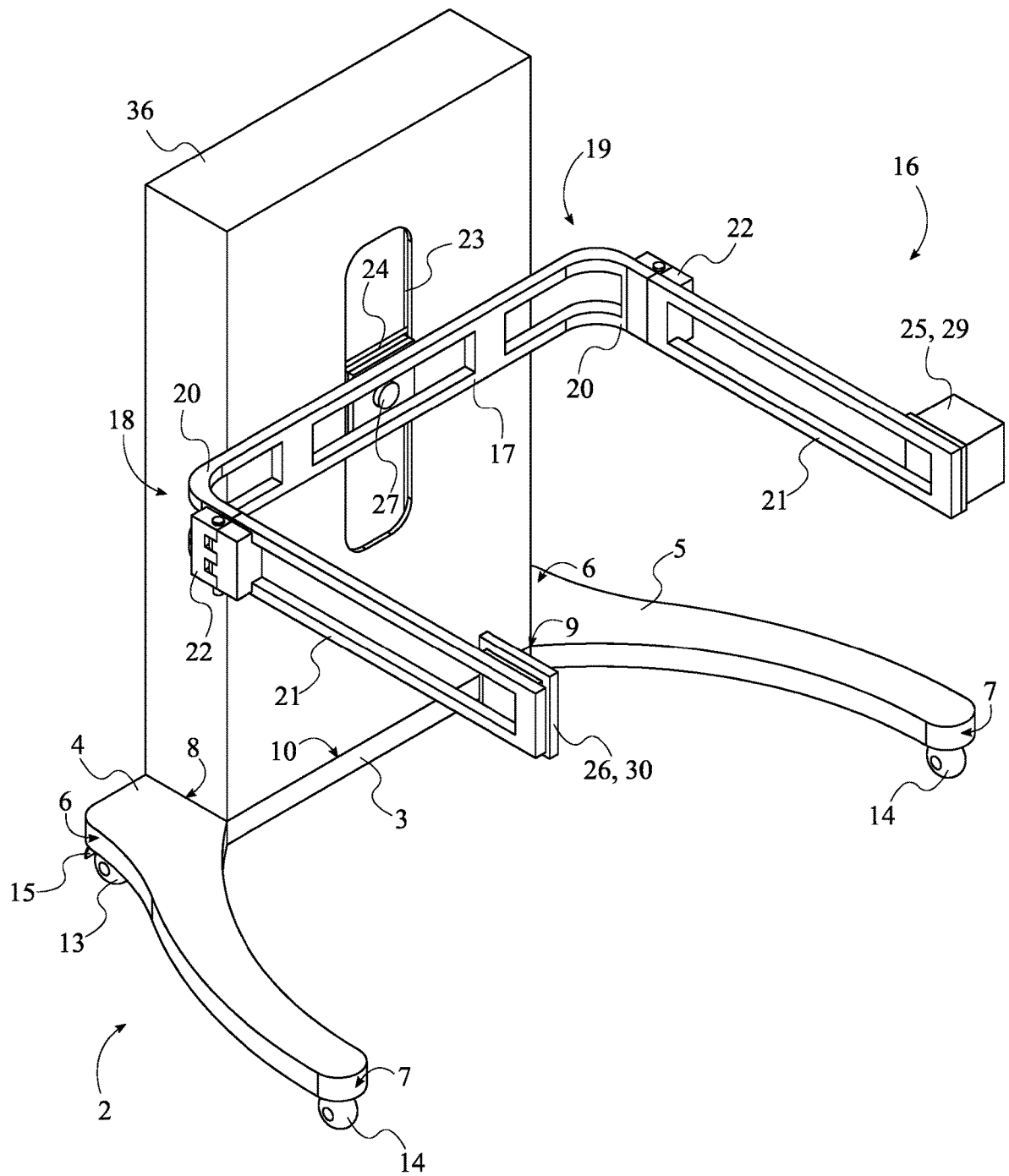
FIG. 4 is a top-front-right perspective view of the present invention, wherein the housing is shown.
Figure 7:
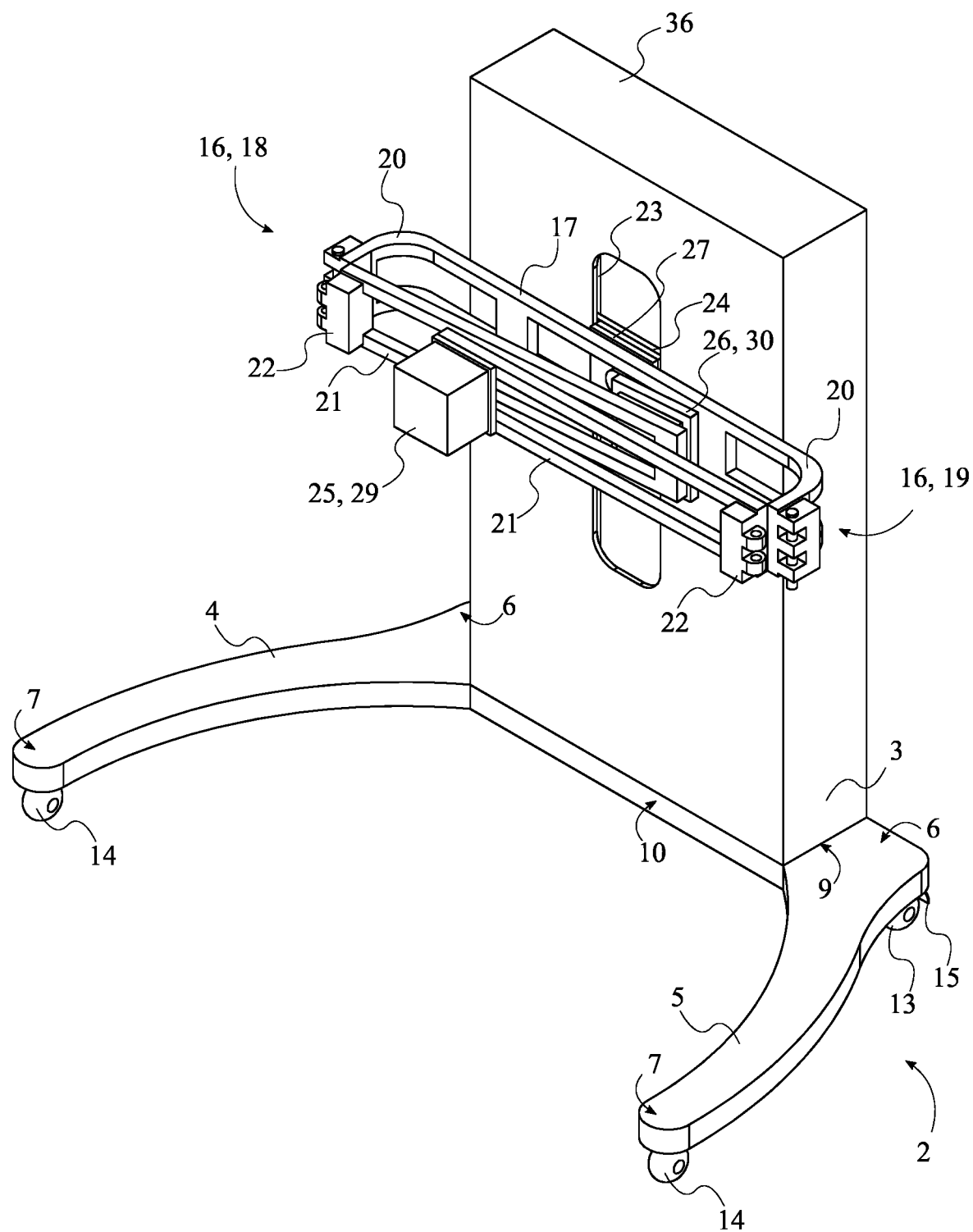
FIG. 7 is a top-front-left perspective view of the present invention, wherein the U-shaped support is shown folded.

To increase the portability of the present invention, the U-shaped support 16 can be designed as a foldable structure to be easily folded up and stowed away in vehicle. The U-shaped support 16 is preferably made from standardized metallic extrusions to allow an operator to rapidly reconfigure or replace portions of the present invention in the field without requiring manufacturer reconditioning or specialized tooling. As can be seen in FIGS. 4 and 7, the first support arm 18 and the second support arm 19 each comprises a proximal arm portion 20, a distal arm portion 21, and a lockable hinge mechanism 22 to enable the folding of each arm for storage and easier mobility of the present invention in tight spaces. The support web 17 is terminally connected to the proximal arm portion 20 to maintain the first support arm 18 and the second support arm 19 connected to the support web 17 by its corresponding proximal arm portion 20. The distal arm portion 21 is terminally positioned to the proximal arm portion 20, opposite to the support web 17, and positioned collinear to the proximal arm portion 20 to form an elongated arm structure. Further, the distal arm portion 21 is rotatably connected to the proximal arm portion 20 by the lockable hinge mechanism 22 to enable the user to fold the U-shaped support 16 for storage or to deploy the U-shaped support 16 to conduct the fluoroscopic procedure. The lockable hinge mechanism 22 enables the user to lock the distal arm portion 21 in the desired position. Alternatively, the lockable hinge mechanism 22 for each arm can be positioned at the connection between the respective arm and the support web 17. In addition, the lockable hinge mechanism 22 maintains calibration even when the first support arm 18 or the second support arm 19 is folded. For example, in a deployed configuration, the distal arm portion 21 is positioned parallel to the proximal arm portion 20 and locked in place to extend the corresponding arm to enable the user to conduct the fluoroscopic procedure. On the other hand, in a stored configuration, the distal arm portion 21 is positioned perpendicular to the proximal arm portion 20, against the support web 17, and locked in place so that the present invention can be transported through tight spaces.

Figure 8:
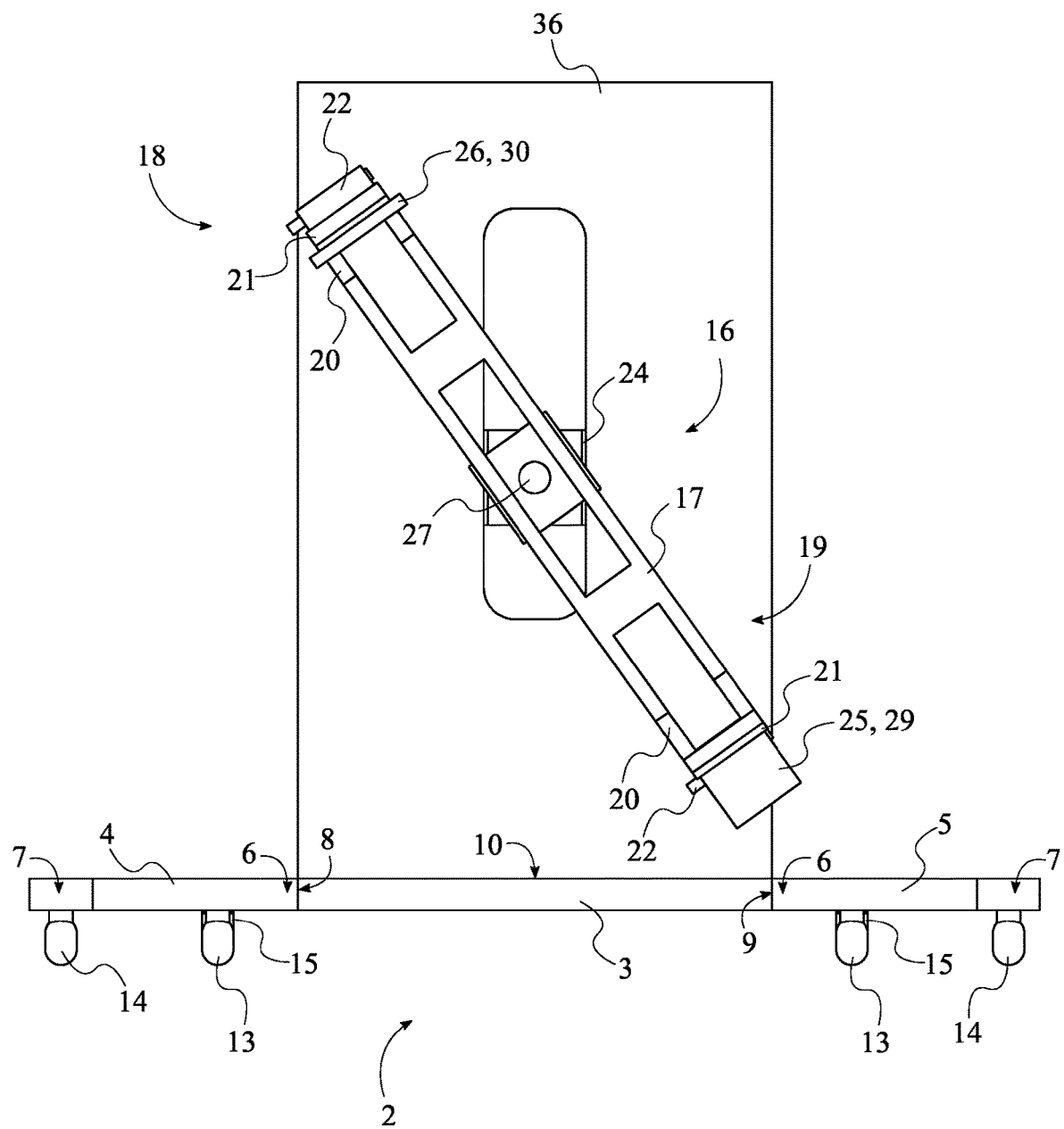
FIG. 8 is a front view of the present invention, wherein the U-shaped support is shown tilted at an angle.

As previously mentioned, the present invention provides various features to accommodate the patient for the fluoroscopic procedure in different locations and positions. As can be seen in FIGS. 3 and 8, the present invention may further comprise a yaw-adjusting mechanism 27 which enables the user to adjust the yaw angle of the U-shaped support 16. The yaw-adjusting mechanism 27 enables the rotation of the U-shaped support 16 on the yaw axis up to an angle, such as twenty degrees, to prevent the present invention from tilting sideways from any momentum. The support web 17 is rotatably connected to the support carriage 24 by the yaw-adjusting mechanism 27 to enable the rotation of the support web 17 about the yaw-adjusting mechanism 27. A rotation axis 28 of the yaw-adjusting mechanism 27 is positioned perpendicular to the support web 17. Likewise, the rotation axis 28 of the yaw-adjusting mechanism 27 is positioned perpendicular to the height-adjusting track 23. Thus, the U-shaped support 16 can be rotated about the support carriage 24 to adjust the yaw angle of the U-shaped support 16 to accommodate patients with different needs. For example, the fully adjustable U-shaped support 16 allows medical staff to test patients who are wheelchair bound, without the need to move the patient from the wheelchair or the bed.

Figure 9:
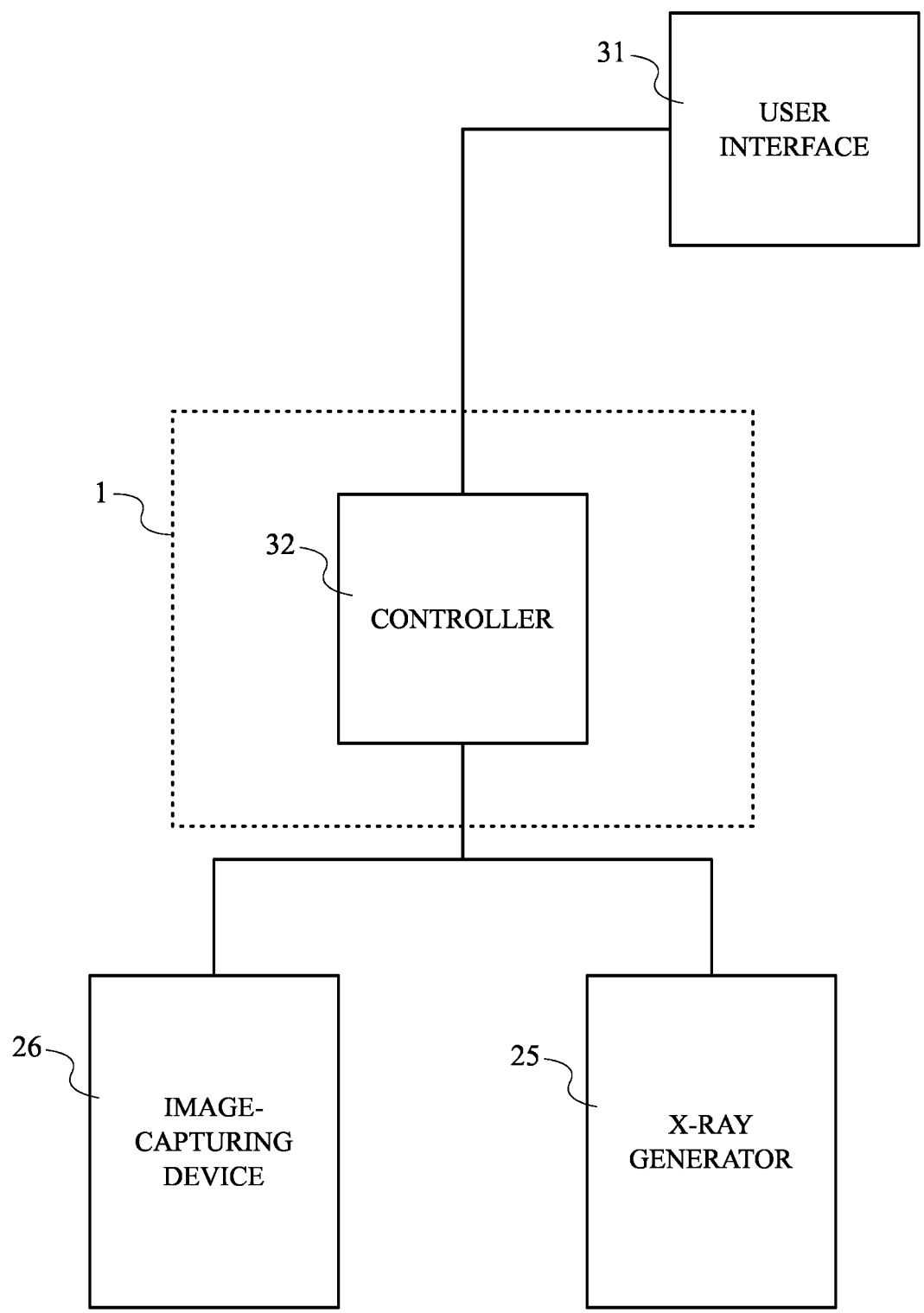
FIG. 9 is a schematic view showing the electronic connections to the controller of the present invention.
Figure 10:
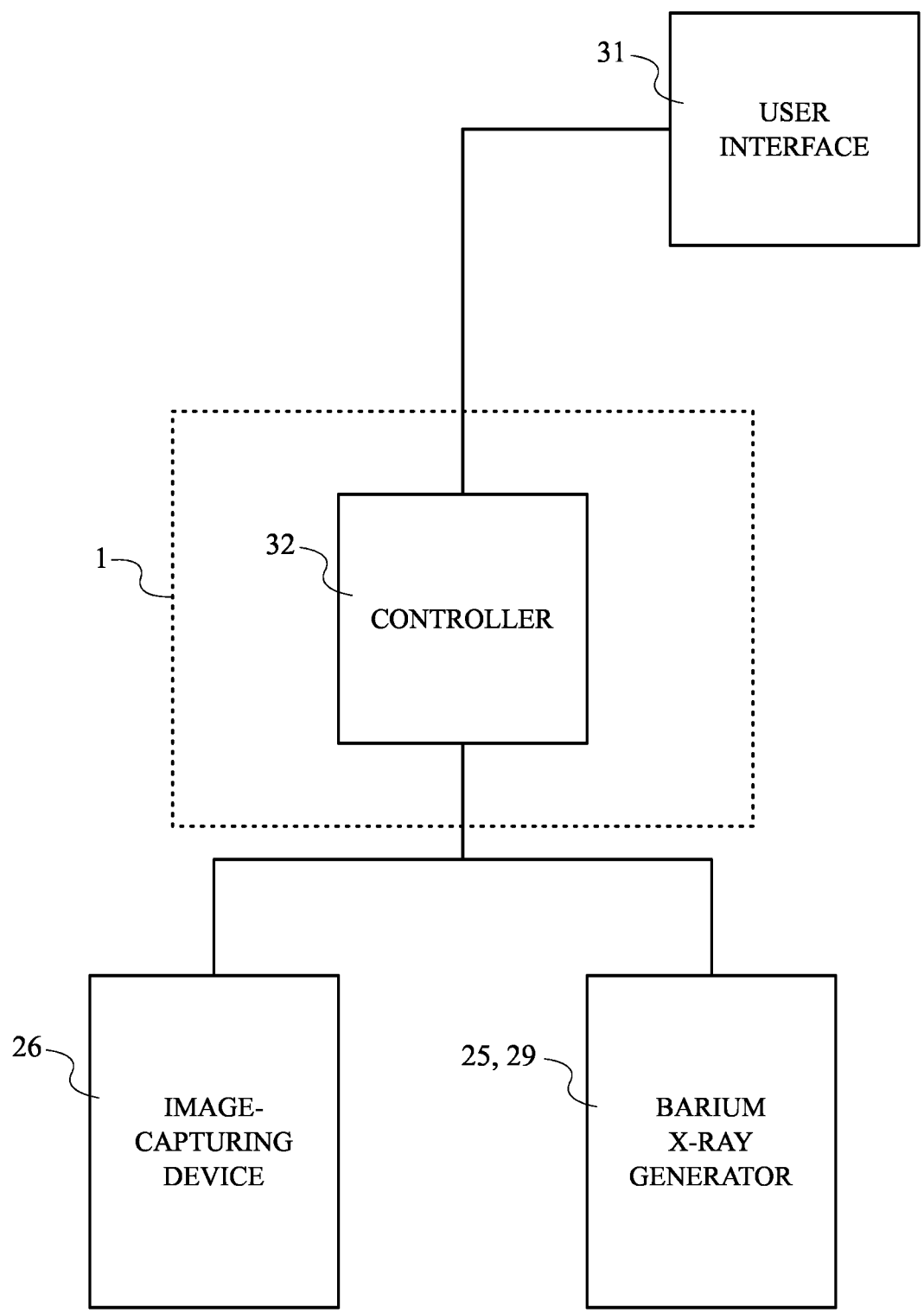
FIG. 10 is a schematic view showing the X-ray generator of the present invention as a barium X-ray generator.
Figure 11:
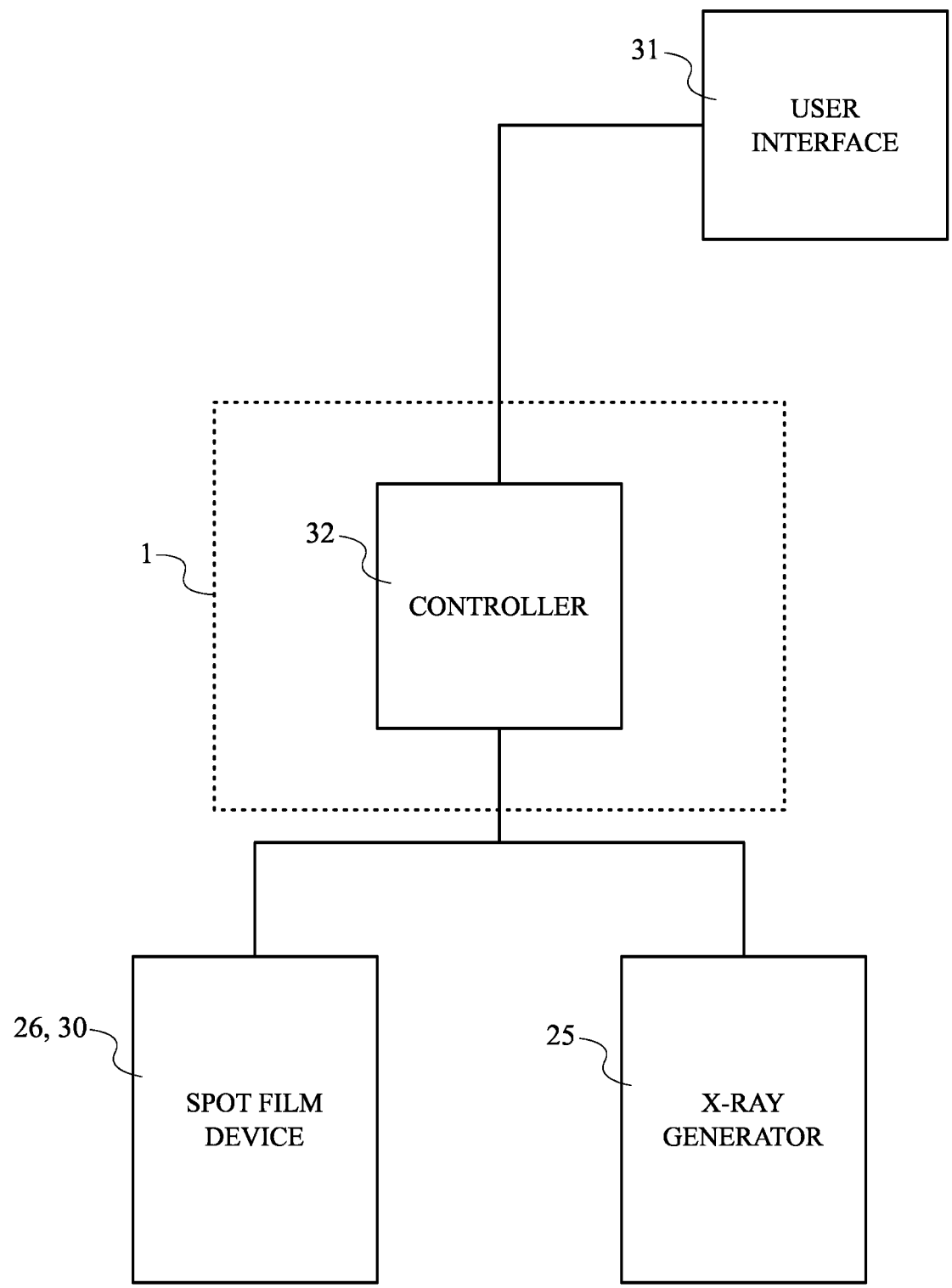
FIG. 11 is a schematic view showing the image-capturing device of the present invention as a spot film device.

To enable the medical staff to perform the necessary fluoroscopic procedure, the present invention can utilize different imaging technologies which can be interchanged as necessary. As can be seen in FIG. 9 through 11, the X-ray generator 25 is preferably a barium X-ray generator 29 to perform barium X-ray examinations of the gastrointestinal (GI) tract. Furthermore, the image-capturing device 26 is preferably a spot film device 30 designed to receive a radiographic film cassette to obtain radiographs during the fluoroscopic procedure. The X-ray generator 25 and the image-capturing device 26 can be set up for either the barium X-ray examination or a fluoroscopy examination. The X-ray generator 25 preferably utilizes a low wattage, pulsed X-ray system for the minimal size, weight, and power requirements of the present invention. In other embodiments, the present invention can utilize different imaging technologies or be connected to external medical devices. In some embodiments, the image-capturing device 26 can utilize other technologies such as a digital radiography (DR) panel designed to digitally capture the X-ray generated data to be transmitted to the user interface 31.

To facilitate the fluoroscopic procedure, the present invention may further comprise a user interface 31 and a controller 32 that enables the medical staff to monitor and control the procedure. As can be seen in FIGS. 1, 2, and 9 through 11, the user interface 31 is laterally mounted to the elongated frame 1, offset from the wheeled base 2, so the user interface 31 does not obstruct with the operation of the present invention. The user interface 31 is also positioned adjacent to a handlebar assembly to provide easy access to the user. Further, the controller 32 is mounted within the elongated frame 1 to protect all electronics from damage. The controller 32 is electronically connected to the user interface 31, the X-ray generator 25, and the image-capturing device 26 so that the controller 32 oversees the operation of the user interface 31, the X-ray generator 25, and the image-capturing device 26. Thus, the user can configure the operation of the X-ray generator 25 and the image-capturing device 26 from the user interface 31 while the controller 32 controls the operation of the image-capturing device 26 and the X-ray generator 25 during the procedure. Further, data from the image-capturing device 26 is transmitted to the controller 32 and the user interface 31 so the user can observe in real time the results of the procedure. In addition, the present invention may include an integral power supply, including a means of integrating external renewable sources of power. In other embodiments, the controller 32 may include a transmitter to wirelessly transmit the procedure data to a remote server.

The present invention may further comprise a foldable arm 33 to reposition the user interface 31 and to keep the medical staff at a safe distance during the fluoroscopic procedure. As can be seen in FIGS. 1 and 2, the foldable arm 33 comprises a proximal arm end 34 and a distal arm end 35.

The proximal arm end 34 is laterally mounted to the elongated frame 1 to secure the foldable arm 33 to the elongated frame 1. Further, the proximal arm end 34 may be positioned in between the height-adjusting track 23 and a handlebar assembly to prevent the foldable arm 33 from obstructing the movement of the U-shaped support 16. The user interface 31 is mounted onto the distal arm end 35 so that the user interface 31 is supported by the foldable arm 33.

Further, to cover the internal structure of the present invention and provide a rugged construction, the present invention may further comprise a housing 36. As can be seen in FIG. 4 through 8, the housing 36 is mounted about the height-adjusting track 23, the support carriage 24, the elongated frame 1, and the support web 17 to provide an aesthetically pleasing look. The housing 36 may include a plurality of housing panels designed to match the shape and design of the corresponding internal components in the height-adjusting track 23, the support carriage 24, the elongated frame 1, and the support web 17. Further, each of the plurality of housing panels may be easily removable for easy maintenance.

Finally, to maintain the U-shaped support 16 at the desired height, the present invention may further comprise a translational locking mechanism 37. As can be seen in FIGS. 1 and 2, the translational locking mechanism 37 is operatively coupled in between the support carriage 24 and the height-adjusting track 23, wherein the translational locking mechanism 37 is used to selectively lock the support carriage 24 at a specific height along the height-adjusting track 23. For example, the translational locking mechanism 37 may be a spring-loaded pin lock that automatically engages with one hole of multiple holes distributed along the height-adjusting track 23. The user can release the spring-loaded pin lock, relocate the U-shaped support 16, and let the spring-loaded pin lock engage with the corresponding new hole. In alternate embodiments, a different translational locking mechanism 37 may be utilized.

Although the invention has been explained in relation to its preferred embodiment, it is to be understood that many other possible modifications and variations can be made without departing from the spirit and scope of the invention.

What is claimed is:
1. A mobile X-ray imaging apparatus comprising:
an elongated frame;
a wheeled base;
a U-shaped support;
a height-adjusting track;
a support carriage;
an X-ray generator;
an image-capturing device;
the wheeled base comprising a base platform, a first bracketing arm, and a second bracketing arm;
the U-shaped support comprising a support web, a first support arm, and a second support arm;
the first bracketing arm being connected adjacent to the base platform;
the second bracketing arm being connected adjacent to the base platform, opposite to the first bracketing arm;
the base platform being terminally mounted to the elongated frame;
the height-adjusting track being laterally mounted along the elongated frame;
the first support arm being terminally connected to the support web;
the second support arm being terminally connected to the support web, opposite to the first support arm;

the support web being movably mounted to the height-adjusting track by the support carriage;

the X-ray generator being laterally mounted to the first support arm, offset from the support web; and, the image-capturing device being laterally mounted to the second support arm, offset from the support web.

2. The mobile X-ray imaging apparatus as claimed in claim 1 comprising:

the base platform comprising a first widthwise edge and a second widthwise edge;

the first bracketing arm and the second bracketing arm each comprising a proximal bracketing end and a distal bracketing end;

the proximal bracketing end of the first bracketing arm being connected adjacent to the first widthwise edge;

the distal bracketing end of the first bracketing arm being positioned offset from the first widthwise edge;

the proximal bracketing end of the second bracketing arm being connected adjacent to the second widthwise edge;

the distal bracketing end of the second bracketing arm being positioned offset from the second widthwise edge; and, the first bracketing arm and the second bracketing arm being positioned adjacent to the U-shaped support.

3. The mobile X-ray imaging apparatus as claimed in claim 2 comprising:

the base platform further comprising a first lengthwise edge; and, the first bracketing arm being oriented at a first obtuse angle with the first lengthwise edge.

4. The mobile X-ray imaging apparatus as claimed in claim 2 comprising:

the base platform further comprising a first lengthwise edge; and, the second bracketing arm being oriented at a second obtuse angle with the first lengthwise edge.

5. The mobile X-ray imaging apparatus as claimed in claim 1 comprising:

a wheel-lock mechanism;

the wheeled base comprising a pair of drive wheels; and, the wheel-lock mechanism being operatively integrated into the pair of drive wheels, wherein the wheel-lock mechanism is used to prevent the rotation of the pair of drive wheels.

6. The mobile X-ray imaging apparatus as claimed in claim 5 comprising:

the wheeled base further comprising a plurality of casters;

the plurality of casters being positioned offset from the pair of drive wheels; and, the plurality of casters being positioned adjacent to the U-shaped support.

7. The mobile X-ray imaging apparatus as claimed in claim 1 comprising:

the first support arm and the second support arm each comprising a proximal arm portion, a distal arm portion, and a lockable hinge mechanism;

the support web being terminally connected to the proximal arm portion;

the distal arm portion being terminally positioned to the proximal arm portion, opposite to the support web; and, the distal arm portion being rotatably connected to the proximal arm portion by the lockable hinge mechanism.

8. The mobile X-ray imaging apparatus as claimed in claim 1 comprising:

a yaw-adjusting mechanism;

the support web being rotatably connected to the support carriage by the yaw-adjustment mechanism;

a rotation axis of the yaw-adjusting mechanism being positioned perpendicular to the support web; and, the rotation axis of the yaw-adjusting mechanism being positioned perpendicular to the height-adjusting track.

9. The mobile X-ray imaging apparatus as claimed in claim 1, wherein the X-ray generator is a barium X-ray generator.

10. The mobile X-ray imaging apparatus as claimed in claim 1, wherein the image-capturing device is a spot film device.

11. The mobile X-ray imaging apparatus as claimed in claim 1 comprising:

a user interface;

a controller;

the user interface being laterally mounted to the elongated frame, offset from the wheeled base;

the controller being mounted within the elongated frame; and, the controller being electronically connected to the user interface, the X-ray generator, and the image-capturing device.

12. The mobile X-ray imaging apparatus as claimed in claim 11 comprising:

a foldable arm;

the foldable arm comprising a proximal arm end and a distal arm end;

the proximal arm end being laterally mounted to the elongated frame, offset from the wheeled base; and, the user interface being mounted onto the distal arm end.

13. The mobile X-ray imaging apparatus as claimed in claim 1 comprising:

a housing; and, the housing being mounted about the height-adjusting track, the support carriage, the elongated frame, and the support web.

14. The mobile X-ray imaging apparatus as claimed in claim 1 comprising:

a translational locking mechanism; and, the translational locking mechanism being operatively coupled in between the support carriage and the height-adjusting track, wherein the translational locking mechanism is used to selectively lock the support carriage at a specific height along the height-adjusting track.

15. A mobile X-ray imaging apparatus comprising:

an elongated frame;

a wheeled base;

a U-shaped support;

a height-adjusting track;

a support carriage;

an X-ray generator;

an image-capturing device;

a yaw-adjusting mechanism;

a housing;

a translational locking mechanism;

a user interface;

a controller;

a foldable arm;

the U-shaped support comprising a support web, a first support arm, and a second support arm;

the foldable arm comprising a proximal arm end and a distal arm end;

the wheeled base comprising a base platform, a first bracketing arm, and a second bracketing arm;

the first bracketing arm being connected adjacent to the base platform;

the second bracketing arm being connected adjacent to the base platform, opposite to the first bracketing arm;

the base platform being terminally mounted to the elongated frame;

the height-adjusting track being laterally mounted along the elongated frame;

the first support arm being terminally connected to the support web;

the second support arm being terminally connected to the support web, opposite to the first support arm;

the support web being movably mounted to the height-adjusting track by the support carriage;

the X-ray generator being laterally mounted to the first support arm, offset from the support web;

the image-capturing device being laterally mounted to the second support arm, offset from the support web;

the support web being rotatably connected to the support carriage by the yaw-adjustment mechanism;

a rotation axis of the yaw-adjusting mechanism being positioned perpendicular to the support web;

the rotation axis of the yaw-adjusting mechanism being positioned perpendicular to the height-adjusting track;

the housing being mounted about the height-adjusting track, the support carriage, the elongated frame, and the support web;

the translational locking mechanism being operatively coupled in between the support carriage and the height-adjusting track, wherein the translational locking mechanism is used to selectively lock the support carriage at a specific height along the height-adjusting track;

the user interface being laterally mounted to the elongated frame, offset from the wheeled base;

the controller being mounted within the elongated frame;

the controller being electronically connected to the user interface, the X-ray generator, and the image-capturing device;

the proximal arm end being laterally mounted to the elongated frame, offset from the wheeled base; and, the user interface being mounted onto the distal arm end.

16. The mobile X-ray imaging apparatus as claimed in claim 15 comprising:

the base platform comprising a first widthwise edge, a second widthwise edge, and a first lengthwise edge;

the first bracketing arm and the second bracketing arm each comprising a proximal bracketing end and a distal bracketing end;

the proximal bracketing end of the first bracketing arm being connected adjacent to the first widthwise edge;

the distal bracketing end of the first bracketing arm being positioned offset from the first widthwise edge;

the proximal bracketing end of the second bracketing arm being connected adjacent to the second widthwise edge;

the distal bracketing end of the second bracketing arm being positioned offset from the second widthwise edge;

the first bracketing arm and the second bracketing arm being positioned adjacent to the U-shaped support;

the first bracketing arm being oriented at a first obtuse angle with the first lengthwise edge; and, the second bracketing arm being oriented at a second obtuse angle with the first lengthwise edge.

17. The mobile X-ray imaging apparatus as claimed in claim 1 comprising:

a wheel-lock mechanism;

the wheeled base comprising a pair of drive wheels and a plurality of casters;

the wheel-lock mechanism being operatively integrated into the pair of drive wheels, wherein the wheel-lock mechanism is used to prevent the rotation of the pair of drive wheels;

the plurality of casters being positioned offset from the pair of drive wheels; and, the plurality of casters being positioned adjacent to the U-shaped support.

18. The mobile X-ray imaging apparatus as claimed in claim 15 comprising:

the first support arm and the second support arm each comprising a proximal arm portion, a distal arm portion, and a lockable hinge mechanism;

the support web being terminally connected to the proximal arm portion;

the distal arm portion being terminally positioned to the proximal arm portion, opposite to the support web; and, the distal arm portion being rotatably connected to the proximal arm portion by the lockable hinge mechanism.

19. The mobile X-ray imaging apparatus as claimed in claim 1, wherein the X-ray generator is a barium X-ray generator.

20. The mobile X-ray imaging apparatus as claimed in claim 1, wherein the image-capturing device is a spot film device.

* * * * *